United States Patent [19]

Johnston

[11] Patent Number: 4,534,906
[45] Date of Patent: Aug. 13, 1985

[54] REMOVAL OF IMPURITIES FROM HUMAN LEUKOCYTE INTERFERON PREPARATIONS

[75] Inventor: Paul D. Johnston, San Mateo, Calif.

[73] Assignee: Genentech, Inc., San Francisco, Calif.

[21] Appl. No.: 438,129

[22] Filed: Nov. 1, 1982

[51] Int. Cl.³ .................... A61K 45/02; C07G 7/00
[52] U.S. Cl. .................................. 260/112 R; 424/85
[58] Field of Search .............. 424/85; 260/112.5 R, 260/112 R; 435/68, 172.3

[56] References Cited

U.S. PATENT DOCUMENTS 4,289,690  9/1981  Pestka et al. ..................... 424/85

OTHER PUBLICATIONS

Stewart II, Interferon and Their Action, pp. 49, 54–56, RC Press Inc., Boca Raton, Florida, 1977.

Primary Examiner—Blondel Hazel

[57] ABSTRACT

Disclosed is a method for removing impurities from leukocyte interferon preparations involving use of a unique incubation procedure.

15 Claims, 10 Drawing Figures

Fig. 1(C).

| Sample | Fast Monomer (mg)‡ | TSK HPLC | | | | SDS-PAGE DENSITOMETRY | | | | |
|---|---|---|---|---|---|---|---|---|---|---|
| | | M | D (Pct.) T | | Te | FM | SM | D (Pct.) T | | Te Other |
| Roche-Prep | 11.0 | 67 | 24.3 | 7.4 | 1.3 | 54.1 | 12.9 | 22.7 | 8.1 | 1.9  0.3 |
| Supernatant | 7.1 | 98.8 | 1.2 | | | 99.8 | 0.2 | 7.5 | 0.2 | |
| Pellet Wash | 0.9 | 94.7 | 5.3 | | | 90.3 | 2.0 | | | |

Fig. 2(C).

| Sample | Fast Monomer (mg)‡ | TSK-HPLC | | | | SDS-PAGE DENSITOMETRY | | | | |
|---|---|---|---|---|---|---|---|---|---|---|
| | | M | D (Pct.) T | | Te | FM | SM | D (Pct.) T | | Te Other |
| Roche-Prep | 0.97 | 67 | 24.3 | 7.4 | 1.3 | 54.1 | 12.9 | 22.7 | 8.1 | 1.9  0.3 |
| Supernatant | 0.4 | >99.9 | | | | 99.9 | 0.1 | | | |
| Pellet Wash | 0.04 | >99.9 | | | | 99.9 | 0.1 | | | |

REMOVAL OF IMPURITIES FROM HUMAN LEUKOCYTE INTERFERON PREPARATIONS

BACKGROUND

The present invention relates to the problem of impurities in preparations of leukocyte interferon which apparently result from the dissociation and reassociation of disulfide bonds during the purification process. Specifically, the invention concerns a novel and effective procedure for removing these impurities from the purified interferon.

Human leukocyte interferon (HuIFN-α) is representative of leukocyte interferons (IFN-α)(s) originally produced by cells from vertebrates of various species which share some degree of sequence homology, e.g. bovine leukocyte interferon and leukocyte interferons from canine, piscine or avian species. HuIFN-α is known to exist in several forms, commonly designated as forms A through K—i.e., for example, HuIFN-αA and HuIFN-αD. Some of these have been expressed in *E. coli* in recoverable quantities as a result of recombinant DNA techniques, and are ordinarily isolated from these cultures by using a monoclonal antibody column as described in Staehlin, et al., *J. Biol. Chem.*, 256: 9750 (1981). It has been found that the interferon so isolated contains contaminants which appear to be products of dissociation and reassociation of disulfide linkages in the native protein. These contaminants are oligomeric forms, which show multiples of the molecular weight of the monomeric protein when subjected to size determination by SDS-PAGE under nonreducing conditions, and also a "slow monomer" which migrates slightly more slowly in SDS-PAGE performed under nonreducing conditions.

One subtype, HuIFN-αA is believed to contain sulfhydryl groups on amino acids numbers 1, 29, 98, and 138. In the native form, the conformation of the molecule corresponds to linkages of these groups from amino acids 1-98, and from 29-138. It is believed that the 29-138 linkage is required for activity, but that activity will be maintained even if the 1-98 linkage is broken. While it is not intended that the invention be construed to depend on any particular theory of origin for the contaminants, it is currently thought that in the case of HuIFN-αA, "slow monomer" is derived from disruption of the 1-98 linkage while the 29-138 linkage remains intact, and the set of oligomers, which are less active, or not active at all, depending on size, represent the binding of one molecule of interferon to another through new disulfide linkages. The presence of the oligomers appears to interfere with the activity of the native HuIFN-αA, the slow monomer is itself active, but may be immunogenic. Therefore, it would be highly desirable to separate the native form from these contaminants.

It has been possible to remove the oligomer from the preparation by gel permeation techniques. However, recovery is not as good as that obtained in the present invention, and, more importantly, the method fails to separate the slow monomer from the native form.

The present invention succeeds in obtaining high yields in isolating the native protein free from both oligomers and slow monomer.

SUMMARY OF THE INVENTION

The invention herein relates to a process for removing slow monomer and oligomers from HuIFN-α preparations and from preparations of other leukocyte interferons characterized by sufficient sequence homology with HuIFN-α by a method which comprises incubating a solution containing IFN-α at a concentration of 1-20 mg/ml and buffered at a pH of between 3 and slightly less than 5 (approximately 4.8), at a temperature of 28°-40° C. The incubation time is 30 minutes to 24 hours. This incubation results in precipitation of the specified unwanted materials, which can then be removed by standard procedures such as centrifugation or filtration.

BRIEF DESCRIPTION OF THE DRAWINGS

FIG. 1 refers to the process of the invention conducted at 32° and a concentration level of 4.2 mg/ml HuIFN-α.

FIG. 2 refers to the process of the invention conducted at 37° and a concentration level of 7.2 mg/ml HuIFN-α.

FIG. 4 shows the separation of oligomers from a HuIFN-α preparation by gel permeation chromatography.

DETAILED DESCRIPTION

A. Definitions

Figure 1A:
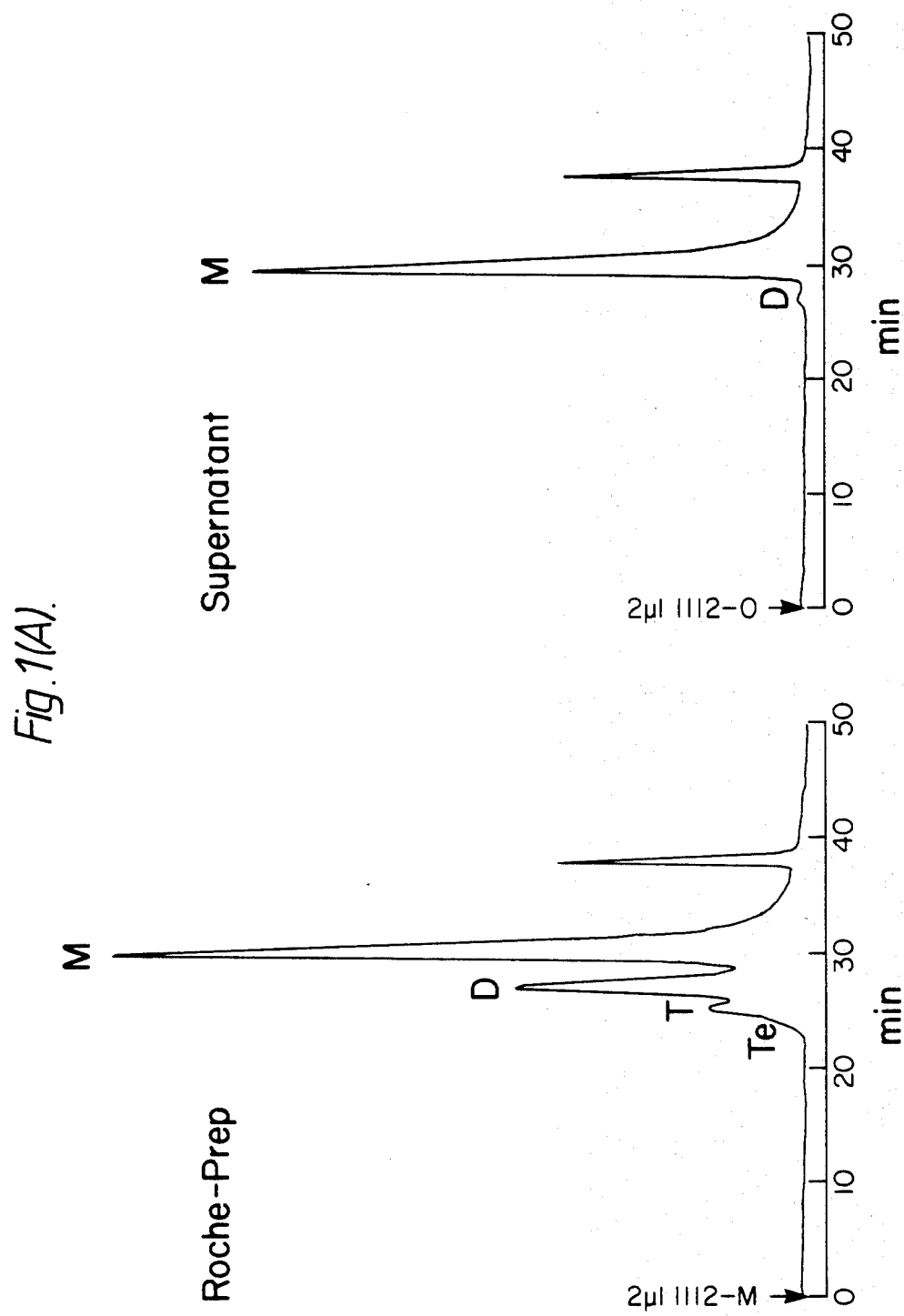
FIGS. 1 and 2 show the analysis, before and after application of the process of the invention, of an HuIFN-α solution using (A) TSK-HPLC and (B) nonreducing SDS-PAGE, quantitated by densitometry. (C) in each figure represents the tabulated data from (A) and (B).
Figure 1B:
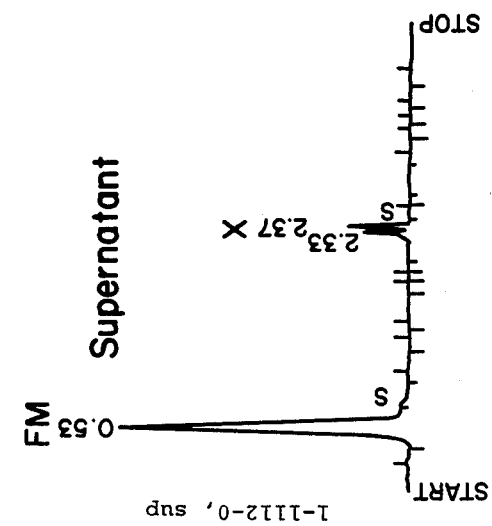
Figure 1B:
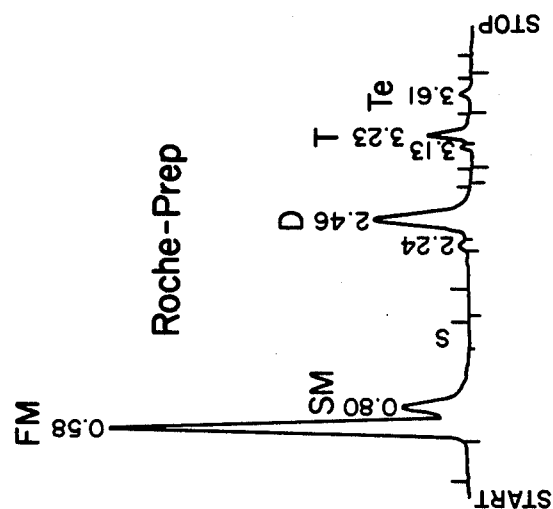
Figure 1B:
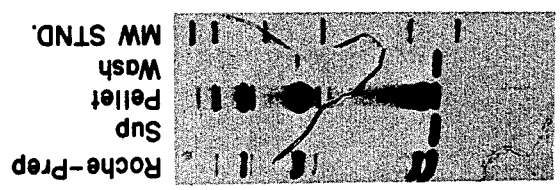
Figure 2A:
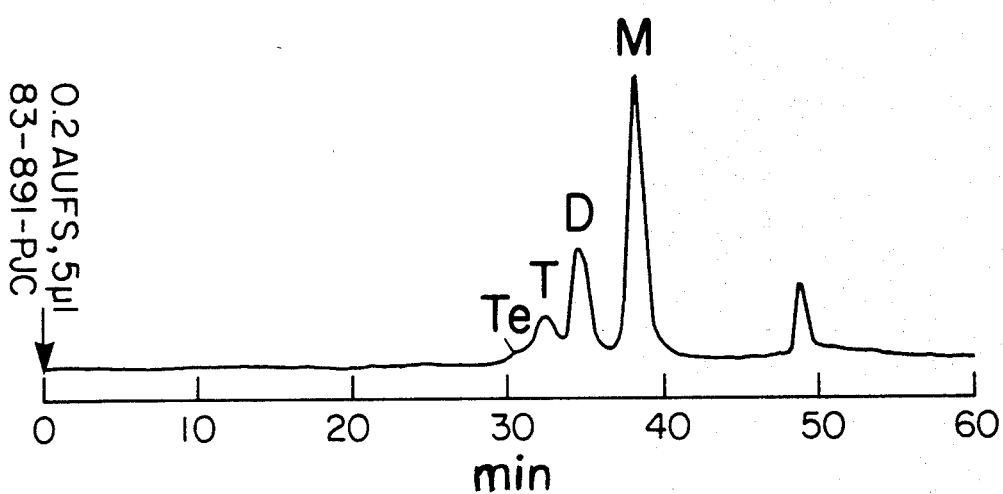
Figure 2A:
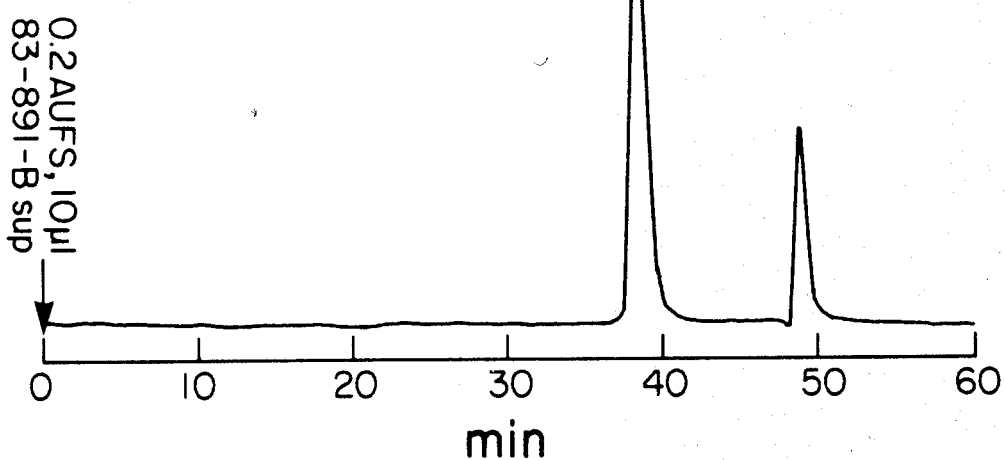
Figure 2B:
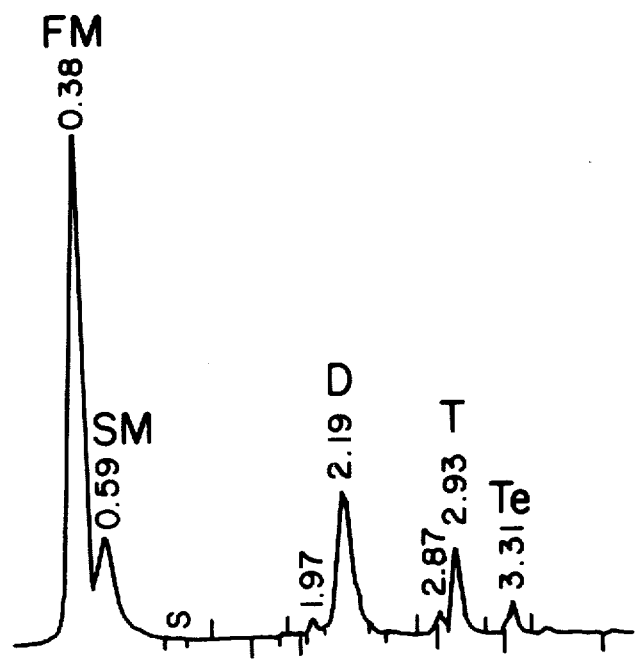
Figure 2B:
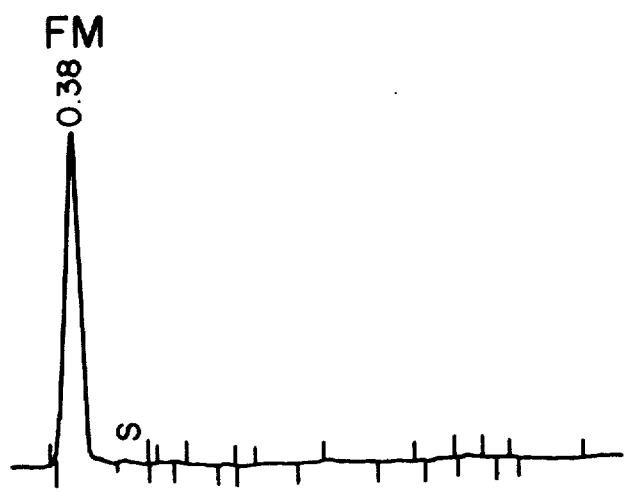

SDS-PAGE (sodium dodecylsulfate polyacrylamide gel electrophoresis) is a electrophoretic technique which resolves substances according to molecular weight. As performed herein, SDS-PAGE is frequently carried out under nonreducing conditions, rather than in the presence of reducing agents, such as e.g. β-mercaptoethanol or dithiothreotol (DTT). These or other such reagents reduce any disulfide bonds to the corresponding sulfhydryl groups. Hence, "nonreducing SDS-PAGE" refers to this technique carried out in the absence of any reducing agent such as β-mercaptoethanol.

This distinction is particularly important to the invention herein, because SDS-PAGE performed under the influence of reducing agent fails to reveal the presence of some of the impurities which are sought to be removed. As more fully set forth in Example 4 herein, when reducing agent is present, certain impurities in the preparation are altered so as to migrate to the same position as native IFN-α. Only when performed under nonreducing conditions, is the presence of these impurities apparent.

"TSK-HPLC" refers to a size separating chromatographic technique employing a molecular seive under high pressure. The acronym results from the tradename of a commercially available gel in combination with HPLC (high performance liquid chromatography).

"HuIFN-α" refers to human leukocyte interferon which is obtained from any source. This interferon, for example, can be isolated from human cells, or from transfected *E. coli* which express HuIFN-α by virtue of recombinant DNA techniques. In any event, HuIFN-α refers to preparations which contain both the "native" form of the protein, and rearrangement products thereof, where these rearrangement products are formed by processes which do not involve altering the amino acid sequence in the interferon. As set forth above, HuIFN-α is currently known to exist as a highly conserved family of proteins, designated alphabetically HuIFN-αA through HuIFN-αK.

"IFN-α", as used herein, refers to leukocyte interferons in general which share sufficient sequence homology with HuIFN-α to be amenable to the process of the invention. Bovine leukocyte interferon is known to have such homology; interferons derived from leukocytes of other species have not been sufficiently studied to ascertain their sequences. However, it is currently thought that homology with HuIFN-α for at least mammalian IFN-α of all species will be sufficient.

"Native IFN-α" refers to that subset of IFN-α which is believed to be three dimensionally substantially identical to that normally produced by the cell. Upon assay by nonreducing SDS-PAGE, native HuIFN-α is associated with a band which corresponds to 17,200 MW as conventionally calibrated. Native IFN-α is also sometimes called "fast monomer", because of its migration in SDS-PAGE in comparison to an impurity—"slow monomer", which is defined below.

"Slow monomer" refers to an IFN-α which behaves aberrantly in nonreducing SDS-PAGE—i.e. HuIFN-α migrates at a calibrated MW of 18,300 daltons, slightly behind the band associated with native HuIFN-α. It is believed this form has been altered in spatial configuration, presumably through rupture of one of the disulfide bonds.

"Oligomers" refers to IFN-α which is partially polymerized. Presumably these condensation products of IFN-α result from formation of disulfide linkages between separate molecules of the monomer. Oligomers include dimers, trimers, tetramers, and higher molecular weight combinations. The oligomers migrate approximately according to their molecular weights in nonreducing SDS-PAGE.

"Impurities" includes the specified oligomers and slow monomer forms of IFN-α as well as other cellular components normally found in association with IFN-α in the host cell or the medium surrounding it. In the present invention, "host cell" includes any leukocyte interferon producing culture including, but not limited to, white blood cells of the appropriate organism and transfected bacteria.

B. General Procedure

The IFN-α preparation which serves as starting material for the process of the invention is prepared, for example, by methods known in the art—e.g. separation by loading on an appropriate antibody column followed by further concentration using known techniques. Any preparation which contains slow monomer and/or oligomers as well as native IFN-α may, of course, be used, regardless of origin.

Preferred starting materials for the process of the invention are mammalian IFN-α, especially HuIFN-α and bovine IFN-α. Particularly preferred is HuIFN-αA, one of the several known forms of human leukocyte interferons.

In the process of the present invention, an IFN-α preparation is brought to a pH between 3 and approximately 4.8, preferably about 3.5–4.2, by titration. The concentration of IFN-α in the preparation (which results from the isolation procedure) is in the range of 1–20 mg/ml, preferably 5–10 mg/ml. The characteristics of proteins in solution, make it desirable to maintain a suitable level of ionic strength in solution to prevent possible denaturations; therefore the IFN-α solution is maintained at a suitable ionic strength by any appropriate salt or salts, such as, for example, ammonium acetate or sodium chloride. A clearly acceptable range of total salt concentration is between 0.01–0.4M, most preferably around 0.1–0.2M, although the outer limits of permissible ionic strength are not clearly defined. Any acceptable salt consistent with the desired pH range may be used. This solution is then incubated at a temperature of 28°–40° C., preferably between about 30°–34° C. for 30 minutes–24 hours, preferably 10–14 hours. A precipitate, which contains slow monomer and the oligomers, is formed. The precipitate is removed by, for example, centrifugation or filtration, preferably centrifugation. The supernatant (or filtrate) then contains substantially pure native IFN-α.

C. Examples

The following examples are intended to illustrate, but not limit the invention.

EXAMPLE 1

Removal of Oligomers and Slow Monomer Impurities from an HuIFN-aA Preparation

HuIFN-αA containing 33 percent oligomers and 12.9 percent slow monomer was obtained from Hoffman-La Roche, Inc. (Roche Prep). The specific activity of this preparation was greater than $1 \times 10^8$ u/mg according to cytophatic effect (CPE) antiviral assays on HeLa and MDBK cells, challenged with vesicular stomatitis virus as described by Wetzel, et al., *J. Interferon Res,* 1: 381 (1981), incorporated herein by reference.

The HuIFN-αA preparation was provided at a concentration of 4.2 mg/ml (as determined by OD at 280 nm) dissolved in 25 mM ammonium acetate, pH 5.0, 0.12M sodium chloride. Five ml of this solution were titrated to pH 4.0 with acetic acid, and incubated for 12 hours at 32° C. with occasional stirring. Precipitate was noticed after ½ hour.

The suspension was centrifuged for 15 minutes at 10,000 rpm and the supernatant recovered, and combined with two washes from the pellets. (Washes were carried out using two hours contact time each).

The combined supernatants were compared to starting material using several criteria. These results are illustrated in FIG. 1:

TSK-HPLC was employed to achieve separation and analysis of monomeric and oligomeric forms of HuIFN-αA. (This technique does not separate fast from slow monomer).

TSK-HPLC was performed using an Altex u-Spherogel TSK 2000 SW column (0.75 by 60 centimeters). 2–10 ug of protein was supplied for injection, and the column was eluted with 0.2M potassium phosphate, pH 6.8 at a flow rate of 0.5 ml/min. Protein was detected by optical density at 214 nm, and the column was calibrated with the molecular weight standards: aldolase 158K, BSA 67K, ovalbumin 45K, and chymotrypsinogen A 25K.

Analysis of the TSK-HPLC results indicated that the supernatant was 98.8 percent in the monomer form, with only 1.2 percent contamination by dimer and with higher molecular weight oligomers absent.

Nonreducing SDS-PAGE conducted according to the method of Laemmli, *Nature,* 277: 680 (1970), incorporated herein by reference, and quantitated using Coomassie Blue stain followed by laser densitometry (LKB 2202 Ultrascan Laser Densitometer with H.P. 3390A Integrator) showed 99.8 percent of the native monomer, 0.2 percent of the slow moving monomer and no oligomer.

Percent yield of native HuIFN-αA was determined by applying a modifying factor to the total protein measured in the supernatant and starting material, respectively. Each was modified by the percent of the total protein attributable to fast monomer as determined by SDS-PAGE as set forth in the previous paragraph. Total protein was determined by optical density measurements at 280 nm assuming an extinction coefficient of 1.06 for a 1 mg/ml solution. The results of these protein assays indicated a 73 percent recovery of native HuIF-αA in the supernatant.

EXAMPLE 2

The procedure of Example 1 was followed using a fresh sample of Roche Prep except that the incubation/precipitation used sample at 7.2 mg/ml containing 1.8 mg protein and 37° C. (See Example 3 for the procedure to alter HuIFN-αA concentration). The results, which are shown in FIG. 2, indicate that the supernatant contained 99.9 percent native HuIFN-αA, with only 0.1 percent slow monomer as a contaminant. However, the percentage yield of the native HuIFN-αA was only 43 percent.

EXAMPLE 3

Comparison of Various Incubation Conditions

The effects of varying incubation time, pH, concentration of HuIFN-αA, and temperature were studied using the basic procedure of Example 1 herein, with the following modifications. (Again, Roche Prep was used; however, a Genentech HuIFN-αA preparation (Genentech Prep) assayed as 86 percent native HuIFN-αA was used in some experiments.)

To vary pH, the preparation was titrated to the desired pH with acetic acid.

In order to vary concentration of HuIFN-αA, the preparation was diluted 2-fold and dialyzed against 25 mM ammonium acetate, pH 4 for 12 hours, then lyophilized, and redissolved in 25 mM sodium acetate, pH 4.0, 0.1M sodium chloride to the desired concentration. Alternatively, if lower concentrations were desired, the solution supplied was diluted directly with 25 mM sodium acetate, pH 4.0, 0.1M sodium chloride. The results of the variation in parameters are shown below for 12 hour incubation times.

presumably due to all forms being reduced (by e.g., β-mercaptoethanol ordinarily used as a reducing agent) to the same form—a monomer containing free sulfhydryl groups.

Figure 3:
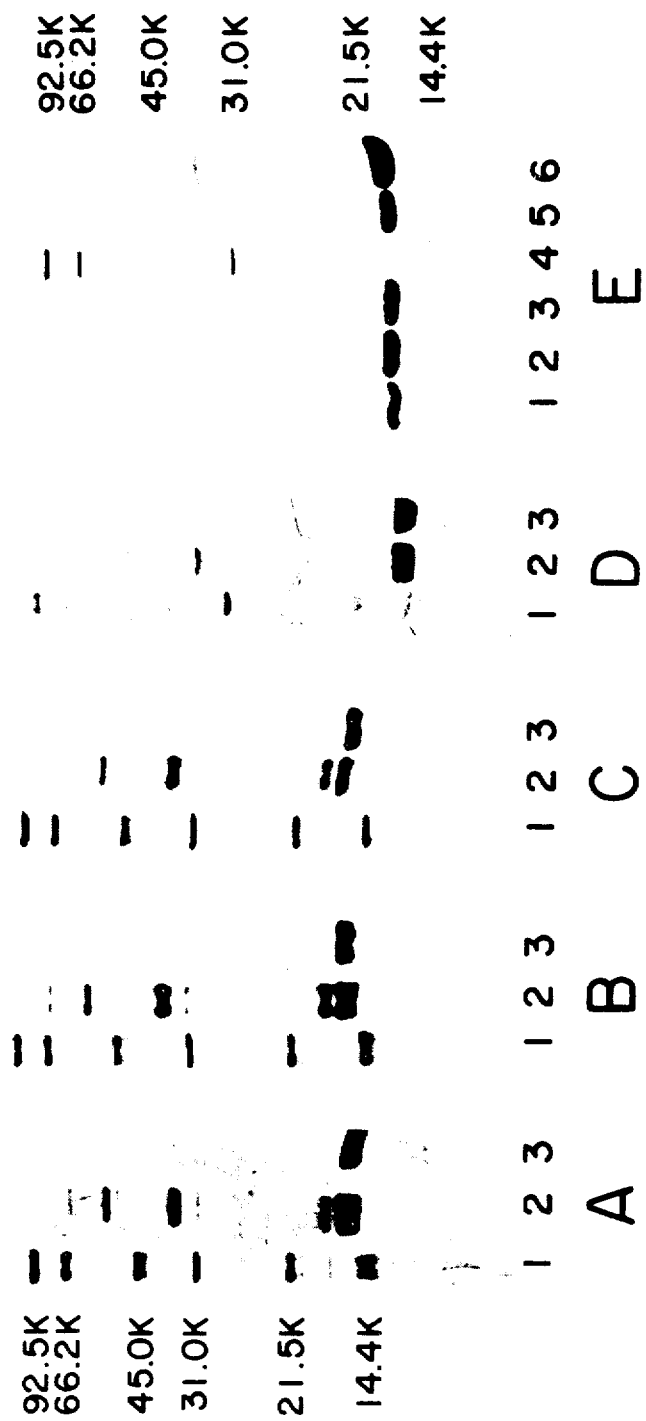
FIG. 3 shows a comparison of the results of reducing and nonreducing SDS-PAGE.

FIG. 3 shows the results of SDS-PAGE under reducing and nonreducing conditions for Roche Prep and the Genentech Prep. Reducing SDS-PAGE shows substantially only the band corresponding to monomer, while nonreducing SDS-PAGE shows a mixture of components.

EXAMPLE 5

Comparison with Gel Permeation Chromatography 0.2 ml of Roche-Prep (4.2 mg/ml) was placed on a 0.7×27 cm column of Sephacryl S300 equilibrated with 50 mM ammonium acetate, pH 4, and eluted at a linear flow rate of 5.2 ml/cm² hour.

The elution pattern and results are shown in FIG. 4.

Part A shows the elution pattern using optical density at 280 nm as a measure of protein. The dotted line portion of the curve represents the interferon activity, and presumably tracks primarily monomeric HuIFN-αA (dimer exhibits about 15 percent of the activity of the monomer).

Part B shows the results of SDS-PAGE under nonreducing conditions of the protein-containing fractions in comparison with starting material. It is evident that separation is not complete in any fraction, although oligomers are concentrated in the earlier fractions. Furthermore, the ratio of slow to fast monomer remains constant in all fractions.

Part C shows a TSK-HLPC trace of fraction 42 which contains predominantly monomeric HuIFN-αA. Again, appreciable amounts of oligomers are still present.

It is thus clear from FIG. 4 that separation of slow monomer does not occur at all, and there is an overlap between the monomer and oligomer fractions, which prevents clean separation.

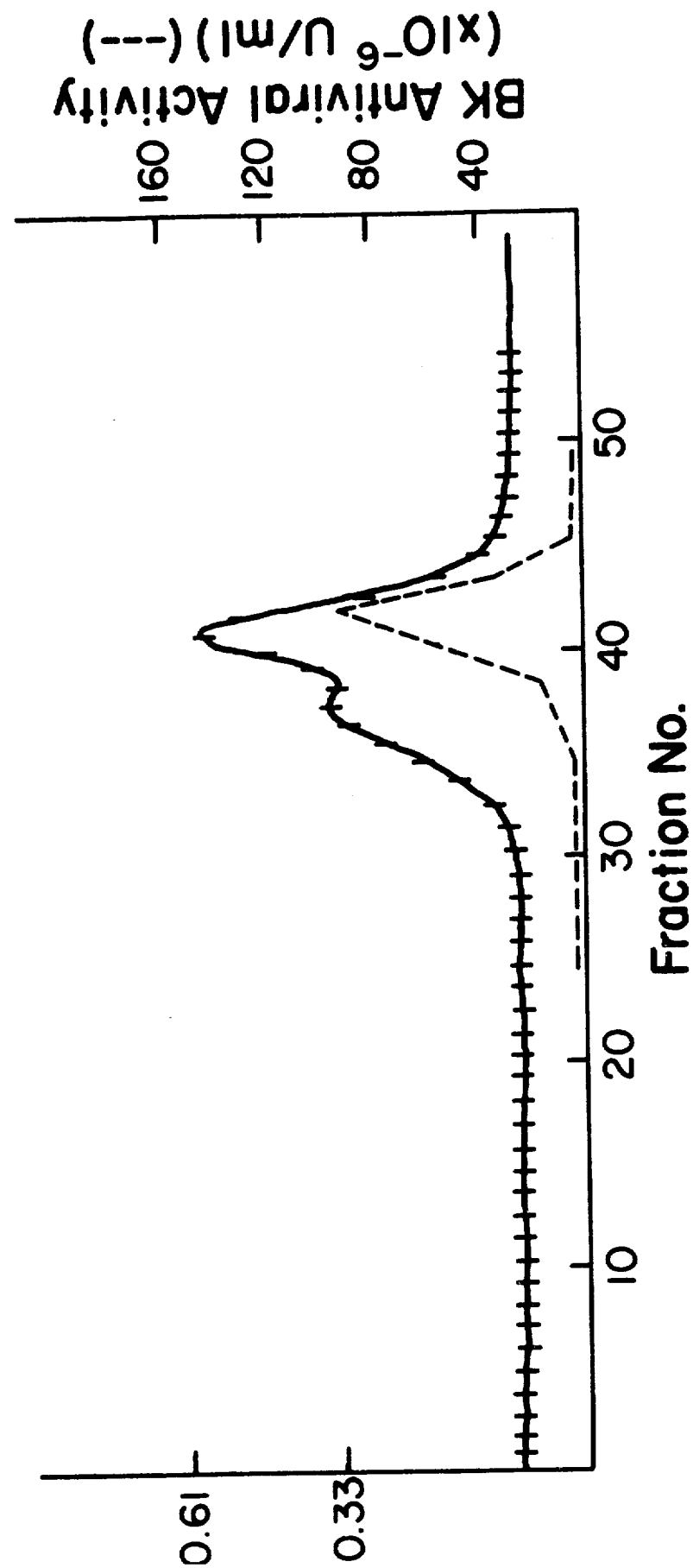

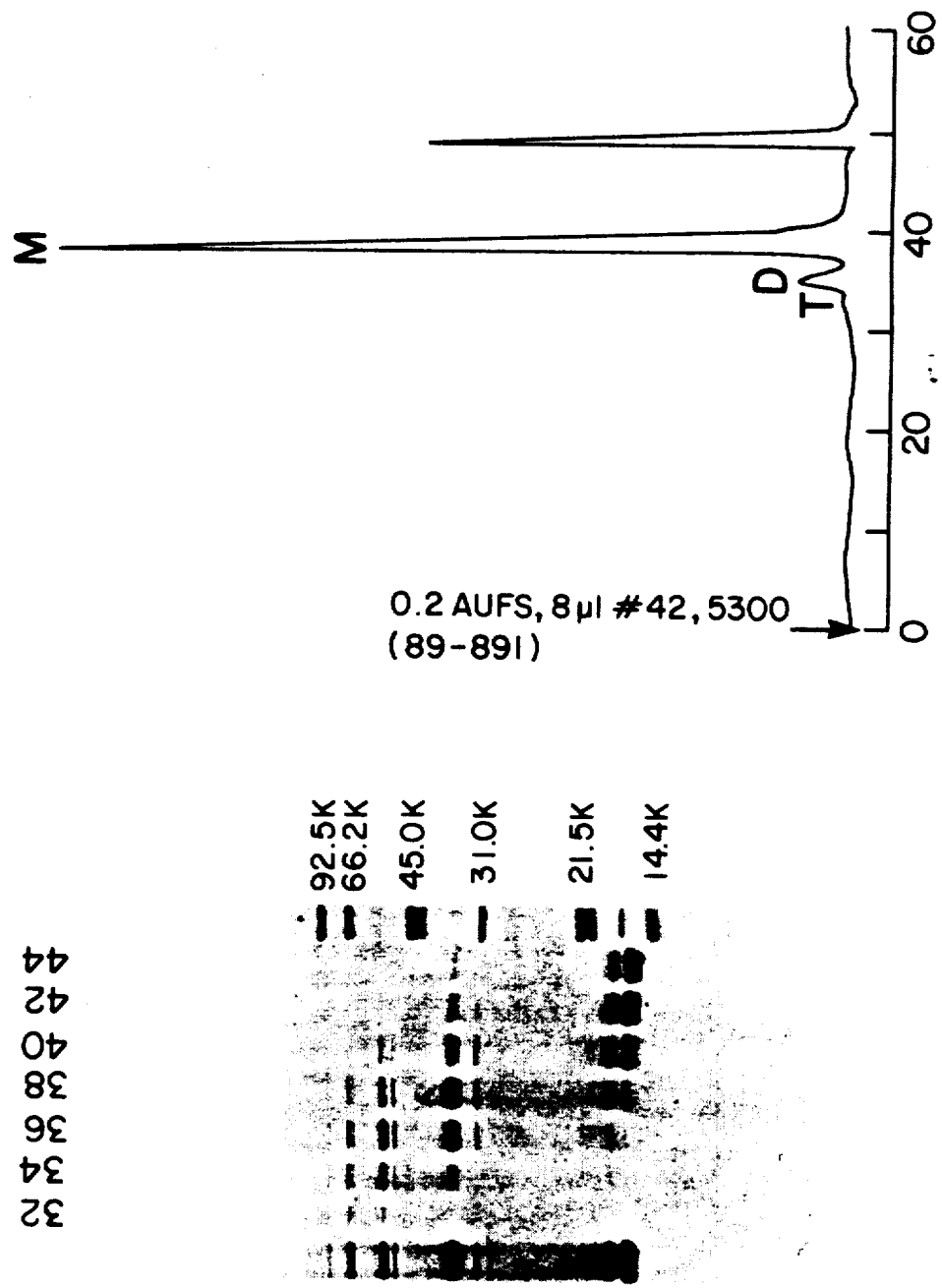

I claim:

1. A method of removing oligomers and slow monomer from leukocyte interferon (IFN-α) having high sequence homology with human leukocyte interferon which method comprises:
   (a) incubating a buffer solution containing 1–20 mg/ml of IFN-α at a pH between 3 and approximately 4.8 for 30 minutes–24 hours at 28°–40° C. to precipitate oligomers and slow monomer followed by;
   (b) recovering native IFN-α.

2. The method of claim 1 wherein the pH is main-

| T | [HuIFN-αA] | Percent Yield+ | SDS-PAGE Percent | | | | TSK-HLPC-Percent | | |
|---|---|---|---|---|---|---|---|---|---|
| | | | Fast M | Slow M | D | T | Monomer | D | T |
| 32° | 7.2 mg/ml | 58 | 99.2 | 0.8 | — | — | 98.5 | 1.5 | — |
| 32° | 4.2 mg/ml | 78 | 98.5 | 1.0 | 0.5 | — | 98.1 | 1.9 | — |
| 37° | 7.2 mg/ml | 59 | 99.9 | 0.1 | — | — | >99.9 | — | — |
| 37° | 4.2 mg/ml | 55 | 99.9 | 0.1 | — | — | 99.8 | 0.2 | — |
| *32° | 10.0 mg/ml | 79 | 99.9 | 0.1 | — | — | 98.7 | 1.3 | — |

*Genentech HuIF-αA preparation.
+Calculated by the formula:
OD 214 of monomer peak on TSK-HPLC (supernatant) × 100 / OD 214 of monomer peak in TSK-HPLC (starting material)

EXAMPLE 4

Comparison of Results with Reducing SDS-PAGE

Failure of SDS-PAGE as ordinarily conducted to detect the oligomeric and slow monomer impurities is tained at about 3.5–4.1.

3. The method of claim 1 wherein the incubation period is about 10–14 hours.

4. The method of claim 1 wherein the incubation temperature is about 30°–34° C.

5. The method of claim 1 wherein the concentration of IFN-α is between about 5–10 mg/ml.

6. The method of claim 1 wherein the native IFN-α is recovered by removing the precipitated oligomers and slow monomer by centrifugation.

7. The method of claim 1 wherein the IFN-α is mammalian IFN-α.

8. The method of claim 1 wherein the IFN-α is human IFN-α.

9. The method of claim 1 wherein the IFN-α is human IFN-αA.

10. The method of claim 1 wherein the IFN-α is bovine IFN-α.

11. A method for removing oligomers and slow monomer from leukocyte interferon (IFN-α) which method comprises:
 (a) incubating a buffer solution containing 5–10 mg/ml of IFN-α at pH between about 3.5–4.1 for about 10–14 hours at about 30°–34° C., to precipitate oligomers and slow monomer followed by;
 (b) recovering native IFN-α.

12. The method of claim 11 wherein the IFN-α is mammalian IFN-α.

13. The method of claim 11 wherein the IFN-α is human IFN-α.

14. The method of claim 11 wherein the IFN-α is human IFN-αA.

15. The method of claim 11 wherein the IFN-α is bovine IFN-α.

* * * * *

UNITED STATES PATENT AND TRADEMARK OFFICE
CERTIFICATE OF CORRECTION

PATENT NO. : 4,534,906
DATED : August 13, 1985
INVENTOR(S) : Paul D. Johnston

It is certified that error appears in the above-identified patent and that said Letters Patent is hereby corrected as shown below:

Insert FIGURES 2B, 3, 4A, 4B and 4C, as part of Letters Patent.

Signed and Sealed this

Twenty-sixth Day of November 1985

[SEAL]

Attest:

Attesting Officer

DONALD J. QUIGG

Commissioner of Patents and Trademarks